(12) United States Patent
Osumi et al.

(10) Patent No.: US 6,194,548 B1
(45) Date of Patent: Feb. 27, 2001

(54) GREEN FLUORESCENT PROTEINS AND BLUE FLUORESCENT PROTEINS

(75) Inventors: Takashi Osumi; Toshiro Tsukamoto; Noriyo Tsukamoto; Masatoshi Yamasaki, all of Hyogo (JP)

(73) Assignee: Takashi Osumi, Hyogo (JP)

( * ) Notice: Subject to any disclaimer, the term of this patent is extended or adjusted under 35 U.S.C. 154(b) by 0 days.

(21) Appl. No.: 09/121,539

(22) Filed: Jul. 24, 1998

(30) Foreign Application Priority Data

Jan. 23, 1998 (JP) .................................................. 10-026418

(51) Int. Cl.[7] .............................. C07K 1/00; C12N 15/00; C07H 21/02

(52) U.S. Cl. ......................... 530/350; 435/440; 536/23.1; 935/10

(58) Field of Search ............................ 530/350; 435/440; 536/23.1; 935/10

(56) References Cited

U.S. PATENT DOCUMENTS

| | | | |
|---|---|---|---|
| 5,491,084 | 2/1996 | Chalfie et al. | 435/189 |
| 5,625,048 | 4/1997 | Tsien et al. | 536/23.4 |
| 5,777,079 | * 7/1998 | Tsien et al. | 530/350 |

FOREIGN PATENT DOCUMENTS

| | | |
|---|---|---|
| 95/21191 | 8/1995 | (WO) . |
| 96/27675 | 9/1996 | (WO) . |
| 97/11094 | 3/1997 | (WO) . |
| 97/42320 | 11/1997 | (WO) . |

OTHER PUBLICATIONS

Chen, C. et al., "High–efficiency Transformation of Mammalian Cells by Plasmid DNA," *Molecular and Cellular Biology*, 7: 2745–2752 (1997).

Heim, R. et al., "Wavelength Mutations and Posttranslational Autoxidation of Green Fluorescent Protein," *Proc. Natl. Acad. Sci. USA*, 91: 12501–12504 (1994).

Heim, R. et al., "Engineering green fluorescent protein for improved brightness, . . ." *Current Biology*, 6: 178–182 (1996).

Siemering, K., "Mutations that suppress the thermosensitivity . . ." *Current Biology*, 6: 1653–1663 (1996).

Tsukamoto, T. et al., *Nature Genetics* 11: 395–401 (1995).

Watanabe, Y., (concise explanation of non–english reference by Watanabe, Y., "Modern Chemistry" *Gendai Kagaku* 12: 46–52 (1995).

Yang, T. et al., "Optimized Codon Usage and Chromophore Mutations . . .", *Nucleic Acids Research*, 24: 4592–4593 (1996).

Palm et al. (May 1997) Nature Structural Biology, vol. 4(5), pp. 361–365.*

Yang et al. (Apr. 3, 1998) J.Biol. Chem., vol. 273, pp. 8212–8216.*

* cited by examiner

Primary Examiner—Ponnathapu Achutamurthy
Assistant Examiner—Elizabeth Slobodyansky
(74) Attorney, Agent, or Firm—Morgan, Lewis & Bockius LLP

(57) ABSTRACT

This invention relates to novel fluorescent GFPs and BFPs. A novel BFP according to this invention has an F64L mutation as well as a L236R mutation and is provided with improved fluorescence. Furthermore, another BFP has the F64L mutation with the characteristics as described above and other mutations, V163A and S175G, and it possesses markedly improved characteristics in the expression at 37° C. in addition to those as described above.

27 Claims, 7 Drawing Sheets

SEQUENCE LISTING

<160> NUMBER OF SEQ ID NOS: 14

<210> SEQ ID NO 1
<211> LENGTH: 238
<212> TYPE: PRT
<213> ORGANISM: Aequorea victoria
<220> FEATURE:
<223> OTHER INFORMATION: Green fluorescent protein

<400> SEQUENCE: 1

```
Met Ser Lys Gly Glu Glu Leu Phe Thr Gly Val Val Pro Ile Leu Val
 1               5                   10                  15

Glu Leu Asp Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Phe
     50                  55                  60

Ser Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125
```

```
                      -continued

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
                180                 185                 190

Val Leu Leu Pro Asp Asn His Tyr Leu Ser Thr Gln Ser Ala Leu Ser
                195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: cloning
      primer

<400> SEQUENCE: 2
tcgtgaccac cttctcccac ggcgtgca                                         28

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: cloning
      primer

<400> SEQUENCE: 3
tgcacgccgt gggagaaggt ggtcacga                                         28

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: cloning
      primer

<400> SEQUENCE: 4
gctggagtac aacttcaaca gccacaacg                                        29

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: cloning
      primer

<400> SEQUENCE: 5
cgttgtggct gttgaagttg tactccagc                                        29

<210> SEQ ID NO 6
<211> LENGTH: 28
<212> TYPE: DNA
<213> ORGANISM: Artificial Sequence
```

```
<220> FEATURE:
<223> OTHER INFORMATION: Description of Artificial Sequence: cloning
      primer

<400> SEQUENCE: 6
cctcgtgacc accctctccc acggcgtg                                          28

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: cloning
      primer

<400> SEQUENCE: 7
cacgccgtgg gagagggtgg tcacgagg                                          28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: cloning
      primer

<400> SEQUENCE: 8
cctcgtgacc accctcacct acggcgtg                                          28

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: cloning
      primer

<400> SEQUENCE: 9
cacgccgtag gtgagggtgg tcacgagg                                          28

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: cloning
      primer

<400> SEQUENCE: 10
gaacggcatc aaggccaact tcaagatcc                                         29

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: cloning
      primer

<400> SEQUENCE: 11
ggatcttgaa gttggccttg atgccgttc                                         29

<210> SEQ ID NO 12
<211> LENGTH: 28
<212> TYPE: DNA
<213> ORGANISM: Artificial Sequence
<220> FEATURE:
```

<223> OTHER INFORMATION: Description of Artificial Sequence: cloning
      primer

<400> SEQUENCE: 12
catcgaggac ggcggcgtgc agctcgcc                                                28

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: cloning
      primer

<400> SEQUENCE: 13
ggcgagctgc acgccgccgt cctcgatg                                                28

<210> SEQ ID NO 14
<211> LENGTH: 239
<212> TYPE: PRT
<213> ORGANISM: Artificial Sequence
<220> FEATURE:
<223> OTHER INFORMATION: Description of Artificial Sequence: Engineered
      green fluorescent protein

<400> SEQUENCE: 14

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Phe Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

GREEN FLUORESCENT PROTEINS AND BLUE FLUORESCENT PROTEINS

BACKGROUND OF THE INVENTION

1. Field of the invention

This invention relates to novel fluorescent proteins, GFPs and BFPs.

2. Related background art

GFP (Green Fluorescent Protein), which was found in Aequorea victoria, is a relatively small protein having a molecular weight of 26,900 and comprising the overall 238 amino acid residues as shown below (SEQ No. 1 in the Sequence Listing).

Therefore, GFP is in use for the visual analysis of gene expression and localization of proteins in a variety of cells in their viable state. However, since such GFP was not luminous at 37° C., there was a problem that culturing must necessarily be done at 30° C. for the purpose of observation in mammalian cells or the like. In connection with this problem, it has been reported that the mutations of V163A and S175G enhance the thermal stability. (K. R. Siemering et al. Curr. Biol. 6, 1653–1663 (1996).)

Recently, a mutant of GFP into which the mutations of Y66H and Y145F were introduced and which had different wavelength characteristics (it is also referred to as "Mutant," and its amino acid sequence is described below with the above-mentioned mutations shown as underlined) was

```
Met Ser Lys Gly Glu Glu Leu Phe Thr Gly Val Val Pro Ile Leu Val
 1           5                  10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
                70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
                115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
                180                 185                 190

Val Leu Leu Pro Asp Asn His Tyr Leu Ser Thr Gln Ser Ala Leu Ser
    195                 200                 205

Lys Asp Pro Asn Glu Lys Arg Asp His Met Val Leu Leu Glu Phe Val
    210                 215                 230

Thr Ala Ala Gly Ile Thr His Gly Met Asp Glu Leu Tyr Lys
225                 230                 235     238
```

In the present specification, the term "GFP protein" refers to a protein that emits green fluorescence when excited by ultraviolet-blue light and that, then, does not require an energy source such as a special substrate or ATP. In other words, the chromophore formation reaction of GFP is autonomous, and the portion of serine-tyrosine-glycine at Nos. 65–67 from the amino terminus forms an imidazolidine ring oxidatively which serves as a chromophore. (Yuichiro Watanabe, Gendai Kagaku "Modern Chemistry" 12, 46–52 (1995); R. Heim et al. Proc. Natl. Acad. Sci. USA 91: 12501–12504 (1994).) Because GFP possesses such a property, a DNA encoding this protein is linked to a suitable expression vector and is introduced into the desired cells to express GFP, which alone results in fluorescent images.

developed. This is referred to as "BFP (Blue Fluorescent Protein)," because it emits blue fluorescence by UV excitation. (R. Heim et al. Curr. Biol. 6, 178–182 (1996); R. Heim et al. Proc. Natl. Acad. Sci. USA 91, 12501–12504 (1994).) In the present specification, the term "BFP protein" refers to a protein that emits blue fluorescence when excited by ultraviolet-blue light and that, then, does not require an energy source such as a special substrate or ATP. However, such BFP had a problem that it experienced severe fading as compared to GFP and was difficult to be observed under a microscope or the like. As used herein to designate mutation, the position of the mutation is expressed by a specific amino acid number in the sequence of the above-mentioned wild type; the amino acid prior to its mutation is described preceding the number and the mutated amino acid is to be described following the number.

Further, amino acids are designated by the one-letter code or three-letter code as appropriate.

```
Met Ser Lys Gly Glu Glu Leu Phe Thr Gly Val Val Pro Ile Leu Val    (SEQ ID NO:2)
 1           5               10                  15

Glu Leu Asp Gly Asp Val Asn Gly His Lys Phe Ser Val Ser Gly Glu
            20              25              30

Gly Glu Gly Asp Ala Thr Tyr Gly Lys Leu Thr Leu Lys Phe Ile Cys
        35              40              45

Thr Thr Gly Lys Leu Pro Val Pro Trp Pro Thr Leu Val Thr Thr Phe
    50              55              60

Ser His Gly Val Gln Cys Phe Ser Arg Tyr Pro Asp His Met Lys Gln
    66          70              75              80

His Asp Phe Phe Lys Ser Ala Met Pro Glu Gly Tyr Val Gln Glu Arg
            85              90              95

Thr Ile Phe Phe Lys Asp Asp Gly Asn Tyr Lys Thr Arg Ala Glu Val
            100             105             110

Lys Phe Glu Gly Asp Thr Leu Val Asn Arg Ile Glu Leu Lys Gly Ile
        115             120             125

Asp Phe Lys Glu Asp Gly Asn Ile Leu Gly His Lys Leu Glu Tyr Asn
    130             135             140

Phe Asn Ser His Asn Val Tyr Ile Met Ala Asp Lys Gln Lys Asn Gly
145             150             155             160

Ile Lys Val Asn Phe Lys Ile Arg His Asn Ile Glu Asp Gly Ser Val
                165             170             175

Gln Leu Ala Asp His Tyr Gln Gln Asn Thr Pro Ile Gly Asp Gly Pro
            180             185             190

Val Leu Leu Pro Asp Asn His Tyr Leu Ser Thr Gln Ser Ala Leu Ser
        195             200             205

Lys Asp Pro Asn Glu Lys Arg Asp His Met Val Leu Leu Glu Phe Val
    210             215             230

Thr Ala Ala Gly Ile Thr His Gly Met Asp Glu Leu Tyr Lys
225             230             235             238
```

SUMMARY OF THE INVENTION

This invention provides novel fluorescent proteins, GFPs and BFPs.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In view of the above-mentioned problems, the present inventors performed extensive research and succeeded in the discovery of novel GFPs and BFPs that are free from such problems by introducing certain mutations into specific positions of the amino acid sequence for GFP or BFP, thus accomplishing this invention.

Specifically, according to this invention, GFP mutants or BFP mutants were prepared from GFP or BFP, either of which was already known (these may be hereinafter referred to as "wild type"), by introducing certain mutations into its specific positions through various techniques. Then, BFP mutants that still emitted brightly after UV radiation for about one hour were obtained among such mutants. In other words, the invention has solved the problem that the conventional BFP experienced severe fading as compared to GFP and was difficult to be observed under a microscope.

Likewise, a mutant of GFP that was brightly luminous even at 37° C. was obtained. Namely, the invention has solved the problem that because the conventional GFP was not luminous at 37° C., its observation in mammalian cells and the like necessitated the need to culture them at 30° C.

Specifically, on the basis of the amino acid sequence for the wild type of GFP (283 amino acid residues, SEQ No. 1 in the Sequence Listing), GFPs into which the mutations as described below had been introduced were prepared, and their fluorescence and thermal characteristics were investigated in this invention.

(1) Phe64Leu
(2) Val163Ala and Ser175Gly were introduced.
(3) Phe64Leu, Val163Ala and Ser175Gly were introduced.

Furthermore, on the basis of the amino acid sequence for the wild type of BFP as described above, GFPs into which the mutations as described below had been introduced were prepared, and their fluorescence and thermal characteristics were investigated in this invention. Here, the mutations introduced were based on the amino acid sequence for the wild type of GFP.

(4) Y66H, Y145F: Phe64Leu, Leu236Arg
(5) Y66H, Y145F: Phe64Leu
(6) Y66H, Y145F: Val163Ala, Ser175Gly
(7) Y66H, Y145F: Phe64Leu, Val163Ala, Ser175Gly, Leu236Arg

Consequently, it was discovered that the resulting BFP and GFP mutants had improved fluorescence characteristics and thermal stability. Specifically, this invention provides novel BFPs and GFPs as will be described below, and further, genes coding them.

1. A GFP protein comprising the amino acid sequence set forth in SEQ ID No. 1 in the Sequence Listing, said sequence having at least mutations of Phe64Leu, Val163Ala, and Ser175Gly.

2. A GFP protein comprising the amino acid sequence set forth in SEQ ID No. 1 in the Sequence Listing, said sequence having the three mutations of Phe64Leu, Val163Ala, and Ser175Gly.

3. A BFP protein comprising the amino acid sequence set forth in SEQ ID No. 1 in the Sequence Listing, said sequence having at least mutations of Y66H, Y145F, and Phe64Leu.

4. A BFP protein comprising the amino acid sequence set forth in SEQ ID No. 1 in the Sequence Listing, said sequence having at least mutations of Y66H, Y145F, Phe64Leu, and Leu236Arg.

5. A BFP protein comprising the amino acid sequence set forth in SEQ ID No. 1 in the Sequence Listing, said sequence having the four mutations of Y66H, Y145F, Phe64Leu, and Leu236Arg.

6. A BFP protein comprising the amino acid sequence set forth in SEQ ID No. 1 in the Sequence Listing, said sequence having at least mutations of Y66H, Y145F, Phe64Leu, Val163Ala, Ser175Gly and Leu236Arg.

7. A BFP protein comprising the amino acid sequence set forth in SEQ ID No. 1 in the Sequence Listing, said sequence having the six mutations of Y66H, Y145F, Phe64Leu, Val163Ala, Ser175Gly and Leu236Arg.

8. A gene encoding the GFP protein according to either Item 1 or Item 2 as described above.

9. A gene encoding the BFP protein according to any of Items 3–7 as described above.

This invention will be illustrated in detail hereinbelow based on its embodiments. The abbreviations of nucleic acids and amino acids (one-letter and three-letter codes) as used in the present specification are set forth below.

(Nucleic Acids)

| | |
|---|---|
| DNA | deoxyribonucleic acid |
| A | Adenine |
| C | Cytosine |
| G | Guanine |
| T | Thymine |

(Amino Acids)

| | |
|---|---|
| Ala (A) | Alanine |
| Arg (R) | Arginine |
| Asn (N) | Asparagine |
| Asp (D) | Aspartic acid |
| Cys (C) | Cysteine |
| Gln (Q) | Glutamine |
| Glu (E) | Glutamic acid |
| Gly (G) | Glycine |
| His (H) | Histidine |
| Ile (I) | Isoleucine |
| Leu (L) | Leucine |
| Lys (K) | Lysine |
| Met (M) | Methionine |
| Phe (F) | Phenylalanine |
| Pro (P) | Proline |
| Ser (S) | Serine |
| Thr (T) | Threonine |
| Trp (W) | Tryptophan |
| Tyr (Y) | Tyrosine |
| Val (V) | Valine |

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DESCRIPTION OF THE PREFERRED EMBODIMENTS

Figure 1:
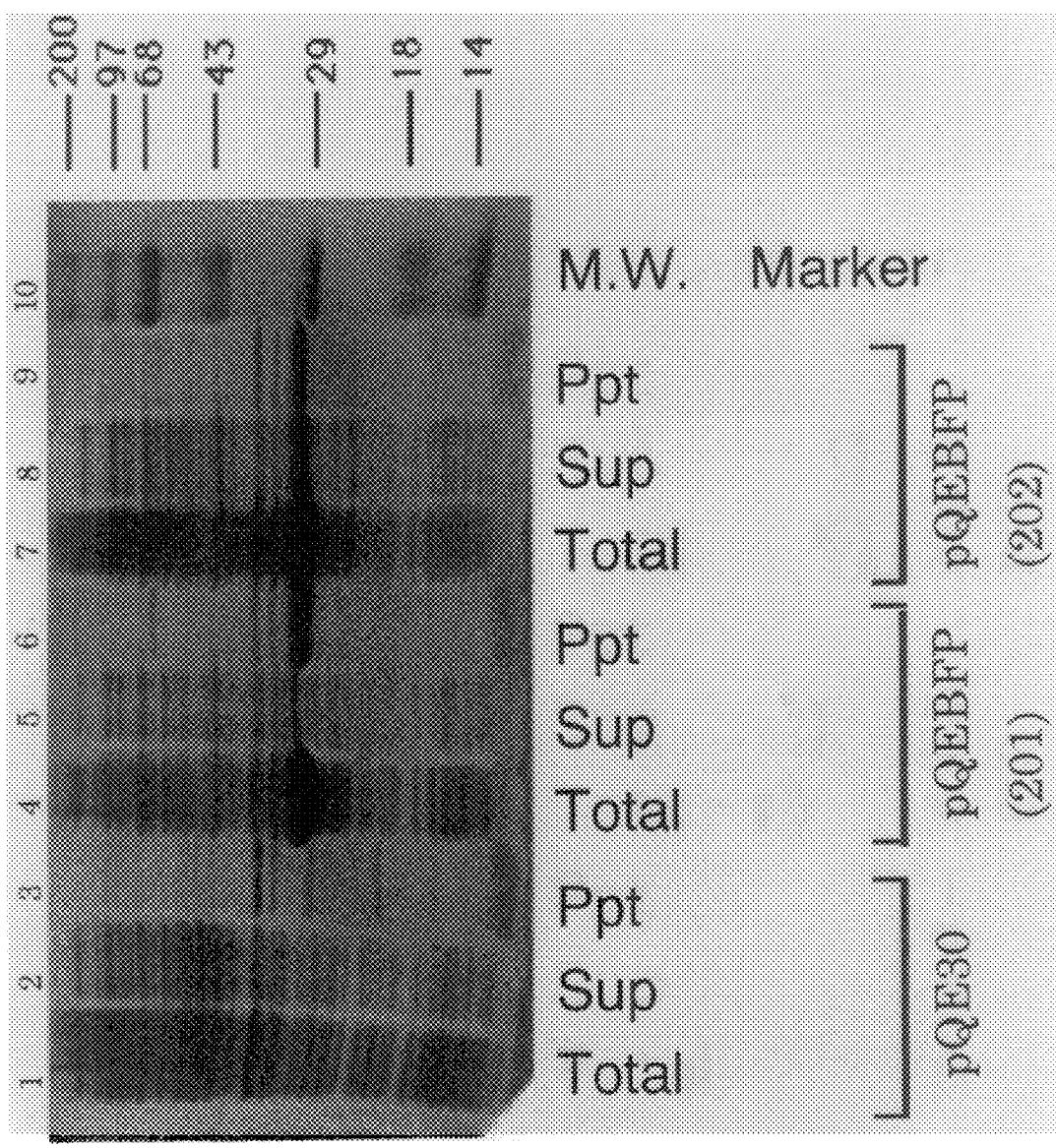
FIG. 1 is an electrophoresis photograph obtained when *E. coli* harboring each plasmid was induced by IPTG and its protein was subjected to SDS-PAGE, where Lanes 1, 4, and 7 show the results of electrophoresis of 50 μl equivalents of the *E. coli* culture media and Lanes 2, 3, 5, 6, 8, and 9 show those of 50 μl equivalents.

Novel GFP or BFP proteins according to this invention are those obtained by introducing certain mutations to parts of the amino acid sequences for the wild types of GFP and BFP, and exhibit improved fluorescence characteristics and thermal stability.

Therefore, this invention embraces proteins having at least such amino acid sequences insofar as they exhibit the improved fluorescence characteristics and thermal stability based on the novel GFP or BFP proteins according to the invention. Namely, in the cases where cells of a variety of origins are used as will be in use in the Examples below, the invention also embraces proteins to which a variety of amino acid sequences other than the aforementioned amino acid sequences are appended at their N- or C-termini and which exhibit the improved fluorescence characteristics and thermal stability based on the novel GFP or BFP proteins according to the invention.

Moreover, this invention provides genes encoding such novel proteins or proteins containing them within parts thereof.

There are no particular limitations to methods for obtaining the novel GFPs or BFPs according to this invention, and methods for artificially obtaining them by means of chemical syntheses and methods for obtaining them according to standard genetic engineering are possible. The latter methods are made possible through the genetic engineering techniques in which suitable vectors conventionally known and means for introducing mutations are combined. Concretely, the following procedure is preferred.

Specifically, the procedure comprises the steps of: (1) starting with a known GFP or BFP protein to be improved and introducing a gene encoding said protein into a suitable vector; (2) introducing mutations into said gene selectively or randomly according to known methods; and (3) selecting desirable mutants on the basis of the fluorescence intensities and temperature-dependence, among others, of the resultant GFP or BFP mutants.

The Contents of Application No.026418/1998, filed on Jan. 23, 1998 in Japan is hereby incorporated by reference.

The above-mentioned procedure will be hereinbelow illustrated in detail by way of examples; however, this invention is not to be limited to these specific examples.

EXAMPLES (I) The genetic engineering techniques as used in the present examples will be illustrated in the following.

1. Vector Construction

In this invention, a DNA portion encoding GFP of pGFP-Cl vector (available from Clontech Inc.) was replaced by a DNA of GFP derived from phGFP-S65T (available from Clontech Inc.), which served as a basic plasmid (hereinafter referred to as "phGFP(101)-Cl"). The vector is meant for expression in mammalian cells and its full base sequence including the vector part is known in the art. The corresponding amino acid sequence is set forth below.

```
Met Val Ser Lys Gly Glu Glu Leu Phe Thr Gly Val Val Pro Ile Leu Val  (SEQ ID NO:14)
 1               5                  10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
    50                  55                  60

Thr Tyr Gly Val Gln Cys Phe Ser Arg Tyr Pro Asp His Met Lys Gln
65                      70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
        130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
        210                 215                 230

Thr Ala Ala Gly Ile Thr Leu Gly Met Asp Glu Leu Tyr Lys
225                 230                 235     238
```

Here, the protein encoded by phGFP-S65T as described above is compared with that of a wild type derived from jellyfish: (i) an amino acid (valine) has been inserted between methionine, which is amino acid number 1 of the amino acid sequence, and serine, which is amino acid number 2; (ii) serine, which is amino acid number 65, has been further mutated to threonine; and (iii) histidine, which is amino acid number 231, has been mutated to leucine. These are respectively underlined in the amino acid sequence as described above. Thus for example, the amino acid number 65 threonine becomes number 66 in reality, but amino acid sequence numbers corresponding to those of the wild type are employed for the amino acid numbers connected with mutation, in accordance with general rules. In other words, the amino acid numbers for the amino acid sequence of the wild type derived from jellyfish (amino acid numbers 1 through 238) are to be used. The extra valine as described above is construed as having been inserted between amino acid number 1 and amino acid number 2, and no number is then designated therefor. In practice, such an addition of valine has been used as a working example to illustrate the embodiments of this invention and it is not the essential amino acid sequence of this invention. Accordingly, in the explanation that follows the presence (or the absence) of the valine addition will not affect the scope of the invention.

Furthermore, methods for introducing specific mutations are not particularly limited, and for example, the method of introduction used in the examples of this invention as described below is feasible. Specifically, a DNA region encoding GFP was cut out from the above-mentioned phGFP(101)-Cl with HindIII, and it was inserted into the HindIII site of a pUC18 vector or a pQE30 vector (Qiagen) to thereby prepare pUCGFP(101) or pQEGFP(101). Here, the pQE30 vector was meant for expression in E. coli.

Employing the resultant pUCGFP(101), pUCBFP(101) into which the mutations of T65S, Y66H, and Y145F had been introduced by the site-directed mutation introduction method as described below was prepared.

Here, through said mutation the amino acid number 65 Ser that was introduced by the above-mentioned mutation (T65S) proved to be identical with the wild type site.

Further, a DNA encoding BFP was cut out from the obtained pUCBFP(201) by digestion with EcoRI/XhoI and it was cloned into the EcoRI/XhoI site of Bluescript II KS(-) (Stratagene) to thereby prepare blueBFP(201).

Furthermore, a DNA region encoding BFP was cut out from the obtained pUCBFP(201) by digestion with HindIII and it was inserted into the HindIII site of a pQE30 vector to thereby prepare pQEBFP(201). On the other hand, phBFP (201)-Cl was prepared by replacing the GFP coding region of the phGFP(101)-Cl vector with the above-mentioned DNA in like manner.

2. Mutagenic Polymerase Chain Reaction (hereinafter referred to as "PCR")

Moreover, methods for randomly introducing mutations are not particularly limited, and Mutagenic PCR as described below can preferably be used in this invention. The Mutagenic PCR can be carried out according to methods known in the art. (C. W. Dieffenbach, ed. PCR PRIMER, A Laboratory Manual (Cold Spring Harbor Laboratory Press) (1995) pp. 583–588.) Concretely, the following conditions were employed in the examples.

About 50 ng of Plasmid BlueBFP(201) was added to 10× mutagenic PCR buffer (70 mM $MgCl_2$, 500 mM KCl, and 100 mM Tris-HCl, pH 8.3 at 25° C.; 0.1%(w/v) gelatin) 10 µl, 10× dNTP (2 mM dGTP, 2 mM dATP, 10 mM dCTP, and 10 mM dTTP) 10 µl, 10 pmol/µl primer (23mer M13Universal primer and M13Reverse primer) 3 µl, and $H_2O$ 62 µl, and mixed. Subsequently, 10 µl of 5 mM $MnCl_2$ was added and mixed, and 1 µl of Taq Polymerase (Takara) was added to conduct PCR (PC-700 available from ASTEC Inc. was used). The PCR was conducted in three tubes under the following conditions: 25 cycles at 94° C. for 1 min, 30 cycles at 45° C. for 1 min, and 35 cycles at 72° C. for 1 min, respectively.

After the respective reaction solutions were combined and treated with chloroform twice, a DNA fragment encoding the amplified BFP was recovered by carrying out electrophoresis on a 1% agarose gel after digestion with BamHI and XhoI and it was inserted into the BamHI and SalI sites of pQE30 (Qiagen Inc.).

Transformation was performed on E. coli JM109, and inoculation was done in a LB medium containing carbenicillin to incubate JM109 at 37° C. for 16 h. Subsequently, the incubated product was allowed to stand at room temperature for 24 h. The E. coli colonies that resulted on a plate were irradiated with UV (Funakoshi UV Transilluminator FTI-201 UV 365 nm) from the top side of the plate for 1 h, and colonies emitting sufficient illumination visually after irradiation were selected: ten colonies were obtained in the example.

Sequence determination was performed on the selected plasmids. With respect to the mutant having mutations within its coding region that appeared meaningful, the coding region was cut out with Hind3 and was inserted into the HindIII site of pQE30, and thereafter, this was cut out with SalI/BglII and replaced by the corresponding portion of pQEBFP to bring the cloning site of the vector into conformity with pQEBFP(201): in the present examples the one prepared from Mutant 10 was designated PQEBFP (202).

3. Construction of Mutant GFP/BFP by the Site-Directed Mutation Introduction Method The site-directed mutation introduction methods are not particularly limited, and for example, the protocol for a Quick Change Kit from Stratagene Inc. was followed. The oligonucleotides shown in Table 2 below were used as primers and the plasmid (about 0.03 µg) obtained by subcloning GFP or BFPcDNA into the HindIII site of a pUC18 or pQE30 vector was used as a template. The concrete PCR conditions are preferably as follows: 16 cycles at 95° C. for 30 sec, 55° C. for 1 min, and 68° C. for 10 min.

TABLE 2

| oligo no. | sequence | |
|---|---|---|
| 1F | TCGTGACCACCTTCTCCCACGGCGTGCA | (SEQ ID NO:2) |
| 1R | TGCACGCCGTGGGAGAAGGTGGTCACGA | (SEQ ID NO:3) |
| 2F | GCTGGAGTACAACTTCAACAGCCACAACG | (SEQ ID NO:4) |
| 2R | CGTTGTGGCTGTTGAAGTTGTACTCCAGC | (SEQ ID NO:5) |
| 3F | CCTCGTGACCACCCTCTCCCACGGCGTG | (SEQ ID NO:6) |
| 3R | CACGCCGTGGGAGAGGGTGGTCACGAGG | (SEQ ID NO:7) |
| 4F | CCTCGTGACCACCCTCACCTACGGCGTG | (SEQ ID NO:8) |
| 4R | CACGCCGTAGGTGAGGGTGGTCACGAGG | (SEQ ID NO:9) |
| 5F | GAACGGCATCAAGGCCAACTTCAAGATCC | (SEQ ID NO:10) |
| 5R | GGATCTTGAAGTTGGCCTTGATGCCGTTC | (SEQ ID NO:11) |
| 6F | CATCGAGGACGGCGGCGTGCAGCTCGCC | (SEQ ID NO:12) |
| 6R | GGCGAGCTGCACGCCGCCGTCCTCGATG | (SEQ ID NO:13) |

TABLE 3

| GFP or BFP used as template | oligo no. used in the introduction of mutation | GFP mutant or BFP mutant after mutation-introduction |
|---|---|---|
| pUCGFP(101) | 1F + 1R | pUCGFP101(+Y66H) |
| pUCGFP101(+Y66H) | 2F + 2R | pUC(201) |
| pQEGFP(101) | 4F + 4R | pQEGFP(103) |

TABLE 3-continued

| GFP or BFP used as template | oligo no. used in the introduction of mutation | GFP mutant or BFP mutant after mutation-introduction |
|---|---|---|
| pQEBFP(201) | 3F + 3R | pQEBFP(203) |
| pQEGFP(101) | 5F + 5R | pQEGFP101(+V163A) |
| pQEGFP101(+V163A) | 6F + 6R | pQEGFP(104) |
| pQEBFP(201) | 5F + 5R | pQEBFP201(+V163A) |
| pQEBFP201(+V163A) | 6F + 6R | pQEBFP(204) |
| pQEGFP(104) | 4F + 4R | pQEGFP(105) |
| pQEBFP(202) | 5F + 5R | pQEBFP202(+V163A) |
| pQEBFP202(+V163R) | 6F + 6R | pQEBFP(205) |

Sequence determination of the resulting plasmids was conducted and it was verified that the desired mutations were contained in the plasmids.

In the examples of this invention, GFPs were designated as 101–105 and BFP were designated as 201–205 for reasons of convenience to place a variety of mutants as obtained in good order. Table 4 below thus summarizes the mutations introduced. Although not shown in the table, GFP 101–105 all contain the mutations of Ser65Thr and His231Leu.

TABLE 4

| GFP | |
|---|---|
| 101 | none |
| 103 | Phe64Leu |
| 104 | Val163Ala, Ser175Gly |
| 105 | Phe64Leu, Val163Ala, Ser175Gly |

| BFP | (as for BFP, the two mutations --Tyr66His (Y66H) and Tyr145Phe (Y14F)--. have been introduced into the sequenee for GFP which serves as a basis) |
|---|---|
| 201 | Y66H, Y145F: |
| 202 | Y66H, Y145F: Phe64Leu, Leu236Arg |
| 203 | Y66H, Y145F: Phe64Leu |
| 204 | Y66H, Y145F: Val163Ala, Ser175Gly |
| 205 | Y66H, Y145F: Phe64Leu, Val163Ala, Ser175Gly, Leu236Arg |

4. Determination of the Quantities of Expression for BFP Mutants

Determination of the quantities of expression for the BFP mutants obtained is not particularly limited, but a comparison of the quantities of their expression in E. coli by means of SDS-PAGE is preferable. Concretely, an overnight culture of E. coli into which each expression vector of pQE30 (empty vector), pQEBF(201), and pQEBFP(202) had been introduced was diluted to 1/50 and it was grown in 3 ml of 2×YT carbenicillin medium at 37° C. for 3 h. IPTG was added to each sample to give its final concentration of 0.24 mg/ml, and the induction of a BFP protein was performed by further culturing the sample for 2.5 h.

An aliquot (100 µl) was taken out from each sample and centrifuged, and precipitates were dissolved in a sample buffer. For each sample, 1.3 ml of E. coli was centrifuged at 10,000 rpm for 1 min and precipitates were suspended in 26091 of PBS(-). This suspension was frozen and thawed at −80° C. for 10 min, and was subjected to ultrasonic treatment (Elma Transonic ultrasonic washer 460/H). Subsequently, it was centrifuged at 15,000 rpm for 5 min to separate soluble proteins from insoluble fractions containing the inclusion body. These were subjected to SDS-PAGE in quantities that correspond to 50 µl cultures of E. coli and were stained with Coomassie Brilliant Blue.

5. Comparison of Brightness of E. coli Cells Having a Variety of GFPs and BFPs Introduced JM109 was transformed with each of pQE30 (empty vector), pQEGFP(101), pQEGFP(105), pQEBFP(201), pQEBFP(202), and pQEBFP(205), and it was streaked on a LB agar medium containing carbenicillin. After incubation at 37° C. for 24 h, the upper lid was removed and the plate was turned upside down and irradiated with UV (Funakoshi UV Transilluminator FTI-201 UV 365 nm to have photographs taken.

6. Transfection of GFP and BFP Mutant cDNAs into CHO Cells by the Calcium Phosphate Method and Fluorescence Measurements A. Transfection Coding regions were cut out from the pQE vectors containing the genes of GFP and BFP mutants that had been prepared by the site-directed mutation introduction method, and the corresponding portions of phGFP(101)-Cl vectors were replaced by them; thus, phGFP(103–105)-Cl and phBFP(202–205)-Cl were prepared.

Unless otherwise so stated, CHO-K1 cells were grown in a F12+10% FBS medium in 5% $CO_2$ at 37° C. The cells ($1\times10^5$) were inoculated into a 6-cm dish, and on the following day, their transfection was conducted in two dishes as a pair by the calcium phosphate method. (C. Chen and H. Okayama Mol. Cell. Biol. 7: 2745–2752 (1987).) After transfection, the one dish was incubated at 37° C. and the other at 30° C. for 24 h. The transfected CHO cells were washed with 1× PBS(-) three times, and they were dissolved in 1 ml of 10 mM Tris-HCl (pH 7.4) containing 1% Triton X-100 and recovered in an Eppendorf tube. A supernatant (0.5 ml) from centrifugation at 3,000 rpm for 5 min was diluted 4-fold with the same buffer and fluorescence measurement was performed. Here, a pUcD2SRαMCS vector (empty vector) was transfected and used as a blank. A Hitachi F-2000 type fluorophotometer was used in the fluorescence measurement. In the measurement of GFPs, fluorescence was scanned between 460 nm and 600 nm at an excitation wavelength of 460 nm to measure the maximal value in the vicinity of the fluorescence wavelength of 510 nm. In the measurement of BFPs, fluorescence was scanned between 360 nm and 500 nm at an excitation wavelength of 360 nm to measure the maximal value in the vicinity of the fluorescence wavelength of 445 nm.

7. Western Blotting

The CHO cells were transfected with pUcD2SRαMCS (empty vector)(T. Tsukamoto et al. Nature Genet. 11: 395–401 (1995)), phGFP(101)-Cl, phGFP(105)-Cl, phBFP (201)-Cl, and phBFP(205)-Cl, respectively and grown at 37° C. and at 30° C. Employing a sample prior to dilution as used in the fluorescence measurement previously described (8 µl), SDS-PAGE was performed on a 12% gel. With the use of a Horizonblot (ATTO Inc.), transfer was conducted onto a nitrocellulose membrane (Millipore Inc., HAHY394FO) under the conditions of 2 mA and 90 min per $cm^2$. After the membrane was taken out and washed with 1× PBS, it was immersed in 1% skim milk/PBS and shaken at room temperature for 30 min. After the membrane was washed with 1× PBS, it was immersed in 0.1% skim milk/PBS containing an anti-GFP antibody (Clonetech Inc.) that had been diluted 2,000-fold and shaken at 4° C. overnight. The membrane was washed with 1× PBS for 5 min, and then with TPBS (0.05% Trion X-100/PBS) for 15 min three times. The membrane was immersed in 0.1% skim milk/PBS containing an anti-rabbit IgG antibody labeled with HRP (Amersham Inc.) that had been diluted 1,000-fold, and shaken at 4° C. for 1 h. The membrane was washed with 1× PBS for 5 min, and then with TPBS (0.05% Trion X-100/PBS) for 15 min three times. The membrane was reacted with a chemiluminescence reagent (Amersham Inc. ECL) for 1 min, and then, was exposed to an X-ray film for 2 min. (II) Amino Acid Sequences of Novel GFP and BFP Mutants

1. Sequence Determination of BFP Mutants

Among the 10 mutants obtained, one mutant (Mutant No. 10) proved that phenylalanine at amino acid number 64, which had been at the immediate N-terminal side of the chromophore, mutated into leucine.

With respect to this mutant clone, another mutation (L236R) had been introduced into its C-terminus (Table 1)

TABLE 1

| mutant no. | mutation |
| --- | --- |
| 1 | L(CTT)1H(CAT) |
| 2 | D(GAT)7Y(TAT) |
| 3 | I(ATC)6T(ACC) |
| 4 | the multicloning site: 14 bp deletion from BamHI |
| 5 | the multicloninq site: 24 bp deletion from BamHI |
| 6 | I(ATC)6N(AAC) |
| 7 | L(CTT)4P(CCT), I(ATC)128G(GTC), D(GAC)197A(GCC), S(AGC)202C(TGC) |
| 8 | L(CTT)4R(CGT) |
| 9 | M(ATG)1T(ACG), Y(TAC)39N(AAC), K(AAG)52E(GAG) |
| 10 | K(AAG)41K(AAA)silent, F(TTC)64L(CTC), L(CTG)236R(CGG) |

With respect to this mutant, BFPcDNA was subcloned into the same HindIII site as in pQEBFP(201) for a comparison purpose to prepare pQEBFP(202).

2. Comparison of the Quantities of Expression for BFP Mutants in E. coli by SDS-PAGE IPTG was added to E. coli cultures harboring pQEBFP (201) and pQEBFP(202) and BFP proteins were allowed to express. When the E. coli cells were irradiated with UV, the E. coli harboring pQEBFP(202) apparently exhibited stronger fluorescence. When the proteins from these E. coli were analyzed by SDS-PAGE, the production of the 31 kDa protein was recognized to almost similar degrees in both E. coli having the respective plasmids (FIG. 1, Lanes 4 and 7).

When the solubility of these BFPs was also studied, BFP(201) with weaker fluorescence was nearly 3;t insoluble (FIG. 1, Lanes 5 and 6), whereas BFP(202) was mostly recovered in the soluble portion (FIG. 1, Lanes 8 and 9).

3. Comparison of Fluorescence of E. coil Cells Having a Variety of GFPs and BFPs Introduced GFPs and BFPs into which the mutations of V163A and S175G had been further introduced in addition to F64L were prepared (see Table 4).

In order to compare the intensities of fluorescence in E. coli, streaking was performed using E. coil cells having an empty pQE30 vector or pQE30 vectors into which cDNAs of GFP101, GFP105, BFP201, BFP202, and BFP205 had been subcloned. The E. coli having the empty vector introduced was not luminous. The E. coli having BFP201 prior to its improvement subcloned, even when irradiated with UV, was hardly luminous. In contrast, the one into which 202 had been subcloned was brightly luminous in blue. Further, it could be ascertained that 205 was even more brightly luminous than was 202.

Figure 2:
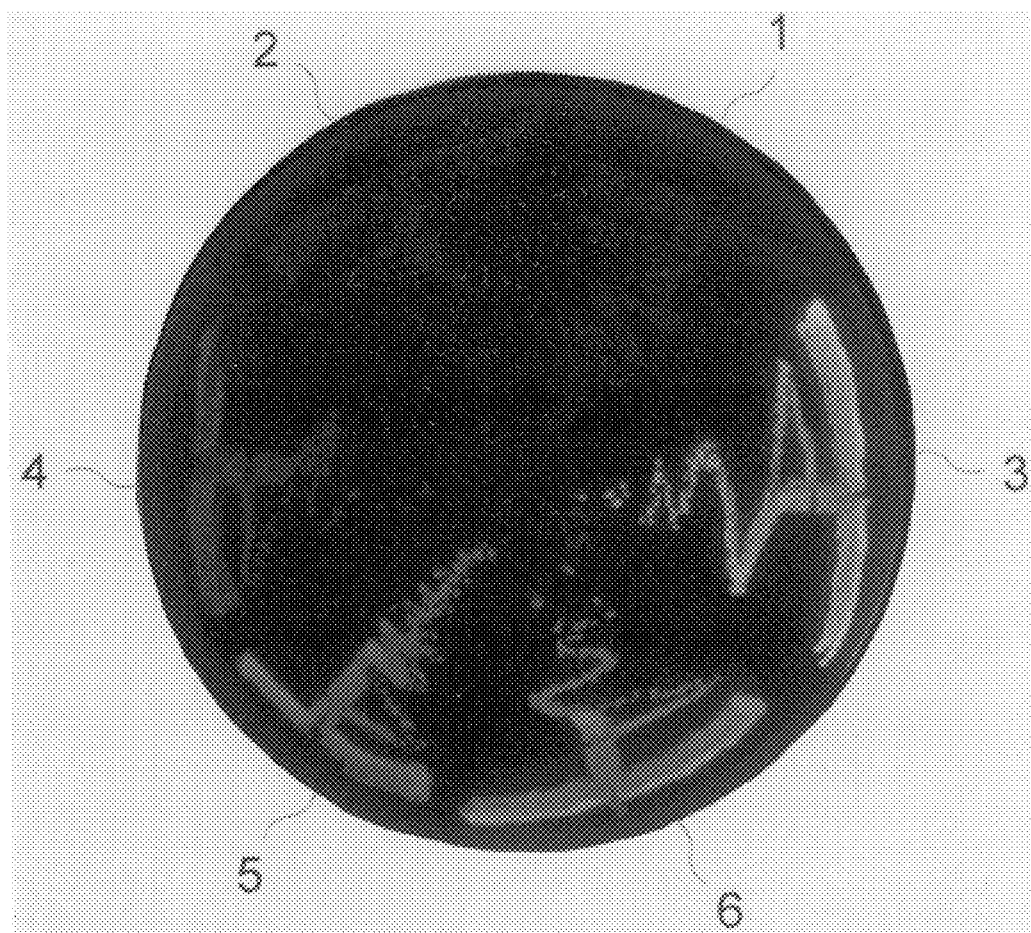
FIG. 2 is a photograph showing the fluorescence emitted when the *E. coli* harboring each plasmid was streaked on a plate, and after culturing at 37° C. overnight, it was irradiated with UV at a long wavelength. "1" indicates empty vector(pQE30), "2" indicates original GFP(pQE101). "3" indicates improved GFP(F64L/V163A/S175G)(pQE105). "4" indicates original BFP(pQE201). "5", indicates improved BFP(F64L/L236R)(pQE202). "6" indicates improved BFP(F64L/V163A/S175G/L236R)(pQE205).

As for GFPs, green fluorescence was observed by the naked eye, and a distinctive difference in brightness was noted between 101 and 105 (FIG. 2).

6. Transfection of GFP and BFP Mutant cDNAs into CHO Cells and Fluorescence Measurements Since very luminous GFPs and BFPs were obtained in E. coli, the comparison was made also in mammalian cells (CHO). The results from the fluorescence measurements of cell extracts that were already prepared under culturing at 37° C. and at 30° C. are summarized (Table 5).

TABLE 5

| GFP or BFP | 37° C. | 30° C. |
| --- | --- | --- |
| 101 | 30.8 | 214.6 |
| 103 | 532.1 | 765.4 |
| 104 | 659.0 | 697.9 |
| 105 | 2991.1 | 868.7 |
| 201 | 14.3 | 166.7 |
| 202 | 304.6 | 188.6 |
| 203 | 331.3 | 210.9 |
| 204 | 330.9 | 265.9 |
| 205 | 901.5 | 287.7 |

The values shown in the table are those obtained by subtracting the value of the empty vector used as a blank from the values of fluorescence obtained. The blank values were 8.9 in the measurement of GFPs at 37° C., 7.14 in the measurement at 30° C., 64.3 in the measurement of BFPs at 37° C., and 50 in the measurement at 30° C.

Table 6 shows relative values when the fluorescence intensity of GFP or BFP prior to its improvement after culturing at 37° C. is taken as 100, and it also makes comparisons in terms of ratio of fluorescence at 37° C. to that at 30° C. From Table 6, BFP(202) having the mutation as found by the Mutagenic PCR exhibited the fluorescence 21 times stronger at 37° C. Further, BFP(202) had two mutations (F64L and L236R); however, BFP(203) having only F64L exhibited a similar intensity of fluorescence to that of 202. This mutation is believed to have caused stronger fluorescence. Seventeen times stronger fluorescence was observed in GFP(103) having F64L.

On the other hand, BFP(204) and GFP(104), both of which had the mutations of V163A and S175G, were brighter 23 times and 21 times, respectively. GFP(105) and BFP(205) in which these mutations were combined with F64L mutation were brighter 97 times and 63 times. In addition, when the ratios of fluorescence intensities at 37° C. to those at 30° C. are taken for comparison, either of 101 and 201 prior to its improvement was darker at 37° C. than at 30° C. Those having F64L alone or the combination of V163A and S175G showed increases in the ratio of fluorescence intensities at two temperatures, whereas it was found that the fluorescence at 37° C. was more than three times brighter with respect to GFP(105) and BFP(205) in which the mutations were combined (Table 6).

TABLE 6

| GFP or BFP | 37° C. | 37° C./30° C. |
| --- | --- | --- |
| 101 | 100 | 0.14 |
| 103 | 1728 | 0.70 |
| 104 | 2140 | 0.94 |
| 105 | 9711 | 3.44 |
| 201 | 100 | 0.09 |
| 202 | 2130 | 1.62 |
| 203 | 2317 | 1.57 |
| 204 | 2314 | 1.24 |
| 205 | 6304 | 3.13 |

6. Examination of the Quantities of Expression in Animal Cells by Means of Western Blotting The CHO cells were transfected with pUcD2SRαMCS (empty vector), phGFP(101)-Cl, phGFP(105)-Cl, phBFP (201)-Cl, and phBFP(205)-Cl, respectively and cultured at 37° C. and 30° C. Employing an anti-GFP antibody for the cultured cells, the quantities of GFP or BFP proteins expressed were examined. About 30 kD bands that were not recognized in the transfection of the empty vector (FIG. 3, Lanes 1 and 6) were detected.

Figure 3:
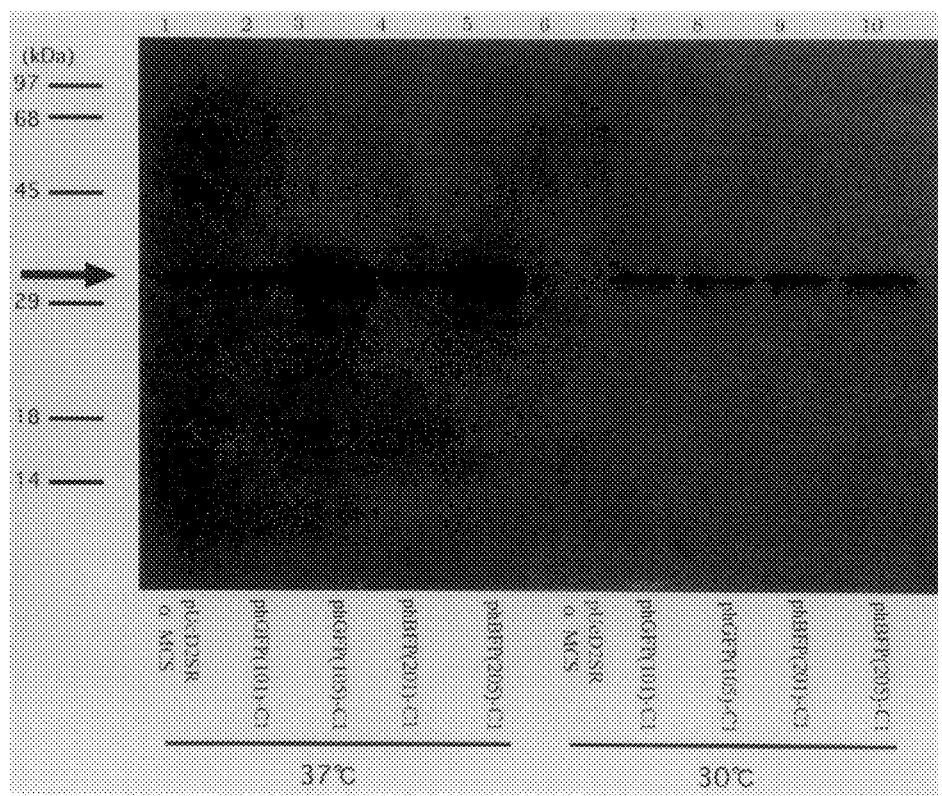
FIG. 3 is an electrophoresis photograph showing the results obtained when CHO cells, after transfection with each plasmid, were cultured at 37° C. or at 30° C., and the culture was subjected to SDS-PAGE followed by transfer onto a nitrocellulose membrane and western blotting with an anti-GFP antibody. Here, the arrow indicates GFP or BFP.

In culturing at 30° C., no distinctive difference was noted between the content of GFP or BFP proteins expressed prior to the introduction of mutations and that after the introduction of mutations (Lanes 7–10). On the other hand, in culturing at 37° C. it was found that the mutants (Lanes 3 and 5) clearly expressed the GFP and BFP proteins in larger quantities (FIG. 3, Lanes 2–5).

The effects associated with the improved BFP and GFP mutants according to this invention are summarized below.

(1) The mutant type BFP(202) obtained by the Mutagenic PCR exhibits enhanced fluorescence as compared to BFP prior to the introduction of mutation in either *E. coli* cells or mammalian cells. In the clone of said mutant BPF, phenylalanine at amino acid number 64 has mutated into leucine (F64L), and further, leucine (amino acid number 236 at the C-terminus) has mutated into arginine (L236R).

With respect to the mutant type BFP(203) having only the mutation at amino acid number 64 as described above, a similar enhancement in fluorescence was also noted in mammalian cells. Therefore, it is F64L that is the responsible mutation for this mutant type BFP(202).

Such a mutation is presumed to involve a mechanism similar to the fluorescence enhancement reported for GFP. (T. -T. Yang et al. Nucleic Acids Res. 24: 4592–4593 (1996).)

(2) The quantities of expression of proteins and the production of soluble proteins were investigated: (i) Although the content of proteins is the same based on the comparison of the quantities of expression of Mutant BFPs in *E. coli* (through SDS-PAGE), the proteins from the mutant type BFP(201) are mostly insoluble whereas soluble proteins have increased in the mutant type BPF(202); and (ii) a large difference in brightness was also seen in *E. coli*.

These results indicate that the mutant type BPF(201) cannot correctly occupy a higher-order structure such as the formation of a chromophore whereas the mutant type BPF(202) tends to occupy a more correct higher-order structure with ease: the mechanism for the above-mentioned fluorescence enhancement is believed to be due to this.

(3) On the other hand, the results of western blotting in the mammalian cells show that the quantity of proteins from GFP or BFP itself has increased. Namely, it is thought that the protein can occupy a stabilized higher-order structure in the mammalian cells; or alternatively, proteolysis becomes slower than that prior to the improvement because the protein structure is stabilized.

(4) With the introduction of the F64L mutation having the characteristics as described above and other mutations, V163A and S175G, GFP and BFP proteins that have markedly improved characteristics in the expression at 37° C. in addition to those as described above are obtained.

Figure 4A:
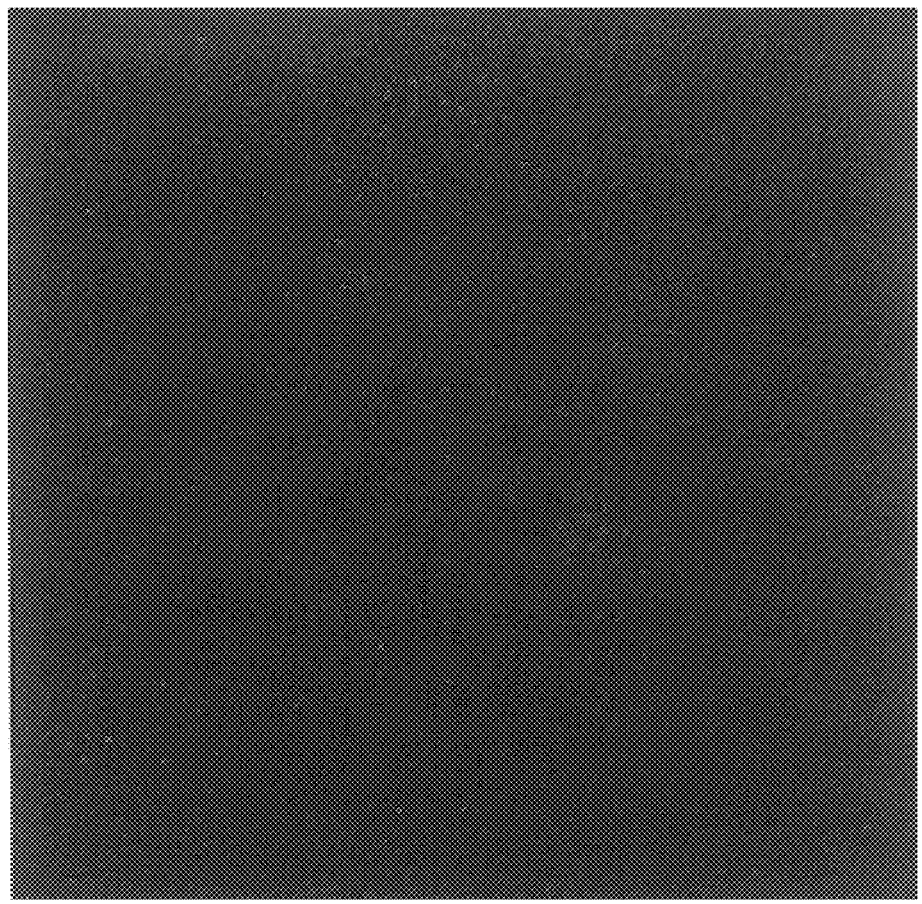
FIGS. 4A and 4B are fluorescence photographs showing the effects associated with the improved type of GFP(B) with the original type of GFP(A).
Figure 4B:
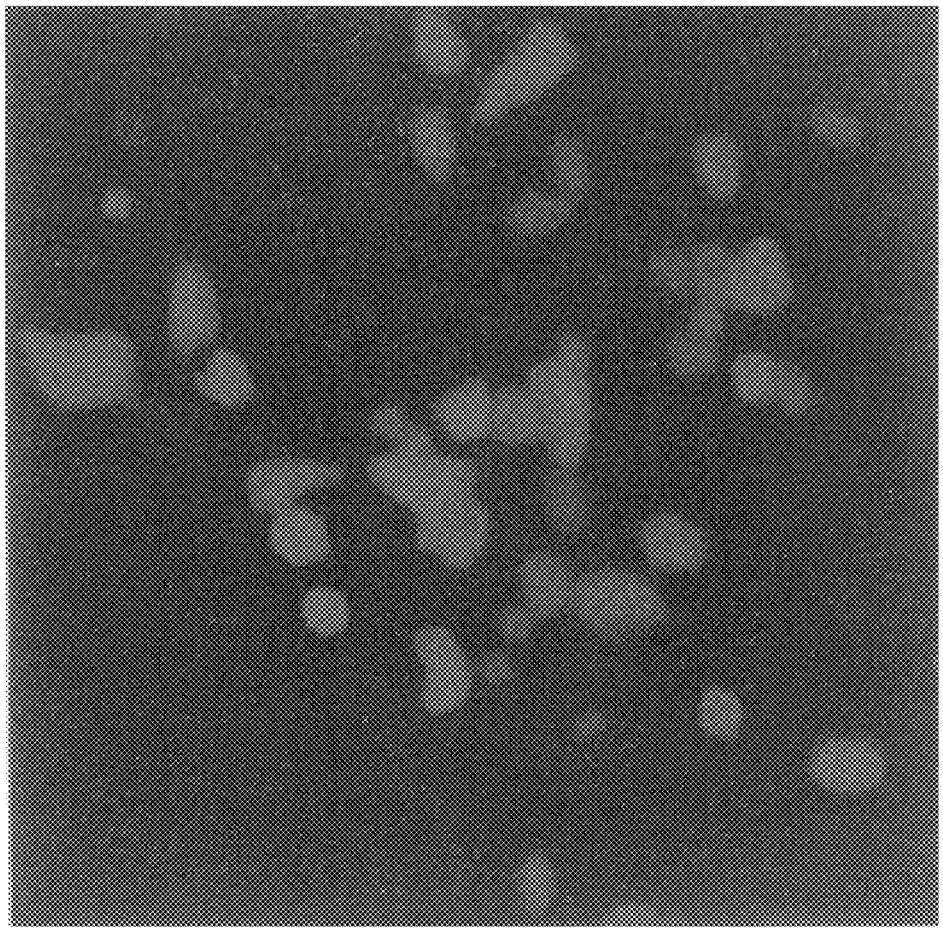
Figure 4C:
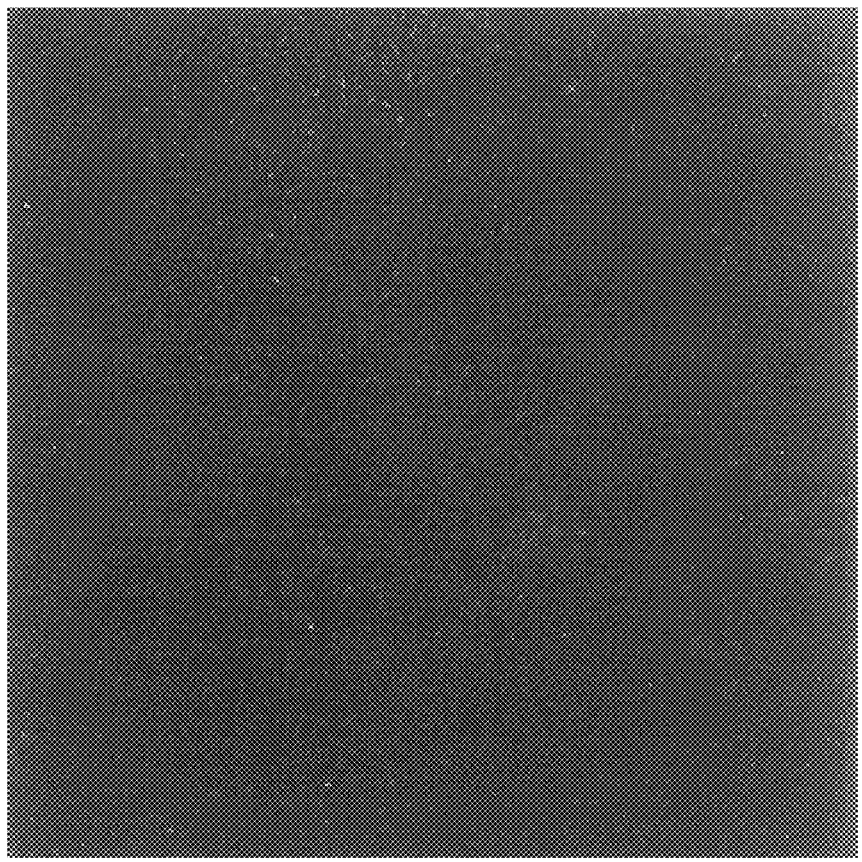
FIGS. 4C and 4D are fluorescence photographs showing the effects associated with the improved type of BFP(D) with the original type of BFP(C).
Figure 4D:

Accordingly, the improved types of GFPs and BFPs into which such mutations have been introduced are provided with the characteristics that will allow them to be brightly luminous even at 37° C., and they will enable observation in the mammalian cells where culturing is to be conducted at 37° C. These improved types of GFPs and BFPs can be applied to cell biology as well as to many research areas. FIGS. 4(A) to (B) show the effects of this invention as described above.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A fluorescent protein comprising the amino acid sequence set forth in SEQ ID No. 1 in the Sequence Listing, said sequence comprising at least mutations of Phe64Leu, Val163Ala, and Ser175Gly.

2. A fluorescent protein comprising the amino acid sequence set forth in SEQ ID No. 1 in the Sequence Listing, said sequence consisting of the three mutations of Phe64Leu, Val163Ala, and Ser175Gly.

3. A fluorescent protein comprising the amino acid sequence set forth in SEQ ID No. 1 in the Sequence Listing, said sequence comprising at least mutations of Tyr66His, Tyr145Phe, Phe64Leu, and Leu236Arg.

4. A fluorescent protein comprising the amino acid sequence set forth in SEQ ID No. 1 in the Sequence Listing, said sequence consisting of the four mutations of Tyr66His, Tyr145Phe, Phe64Leu, and Leu236Arg.

5. A fluorescent protein comprising the amino acid sequence set forth in SEQ ID No. 1 in the Sequence Listing, said sequence comprising at least mutations of Tyr66His, Tyr145Phe, Phe64Leu, Val163Ala, Ser175Gly and Leu236Arg.

6. A fluorescent protein comprising the amino acid sequence set forth in SEQ ID No. 1 in the Sequence Listing, said sequence consisting of the six mutations of Tyr66His, Tyr145Phe, Phe64Leu, Val163Ala, Ser175Gly and Leu236Arg.

7. A fluorescent protein of SEQ ID NO:1 comprising at least mutations of Tyr66His, Tyr145Phe, Val163Ala and Ser175Gly.

8. A fluorescent protein of SEQ ID NO:1 consisting of mutations of Tyr66His, Tyr145Phe, Val163Ala and Ser175Gly.

9. A fluorescent protein comprising the amino acid sequence set forth in SEQ ID No. 1 in the Sequence Listing, said sequence consisting of mutations of Tyr66His, Tyr145Phe, and Phe64Leu.

10. The protein of claim 1 further comprising one or more mutations selected from the group consisting of Ser65Thr, His231Leu and a valine inserted between Met1 and Ser2.

11. The protein of claim 3 further comprising one or more mutations selected from the group consisting of Ser65Thr, His231Leu and a valine inserted between Met1 and Ser2.

12. The protein of claim 5 further comprising one or more mutations selected from the group consisting of Ser65Thr, His231Leu and a valine inserted between Met1 and Ser2.

13. The protein of claim 7 comprising one or more mutations selected from the group consisting of Ser65Thr, His231Leu and a valine inserted between Met1 and Ser2.

14. A fluorescent protein comprising the amino acid sequence set forth in SEQ ID No. 1 in the Sequence Listing, said sequence consisting of mutations of Phe64Leu, Val163Ala, and Ser175Gly and one or more mutations selected from the group consisting of Ser65Thr, His231Leu and a valine inserted between Met1 and Ser2.

15. A fluorescent protein comprising the amino acid sequence set forth in SEQ ID No. 1 in the Sequence Listing, said sequence consisting of mutations of Tyr66His, Tyr145Phe, Phe64Leu, and Leu236Arg and one or more mutations selected from the group consisting of Ser65Thr, His231Leu and a valine inserted between Met1 and Ser2.

16. A fluorescent protein comprising the amino acid sequence set forth in SEQ ID No. 1 in the Sequence Listing, said sequence consisting of mutations of Tyr66His, Tyr145Phe, Phe64Leu, Val163Ala, Ser175Gly and Leu236Arg and one or more mutations selected from the group consisting of Ser65Thr, His231 Leu and a valine inserted between Met1 and Ser2.

17. A fluorescent protein comprising the amino acid sequence set forth in SEQ ID No. 1 in the Sequence Listing, said sequence consisting of mutations of Tyr66His, Tyr145Phe, Val163Ala and Ser175Gly and one or more mutations selected from the group consisting of Ser65Thr, His231Leu and a valine inserted between Met1 and Ser2.

18. A fluorescent protein comprising the amino acid sequence set forth in SEQ ID No. 1 in the Sequence Listing, said sequence consisting of mutations of Tyr66His, Tyr145Phe, and Phe64Leu and one or more mutations selected from the group consisting of Ser65Thr, His231Leu and a valine inserted between Met1 and Ser2.

19. The protein of claim 1, further comprising one or more mutations selected from the group consisting of His231Leu and a valine inserted between Met1 and Ser2.

20. The protein of claim 3, further comprising one or more mutations selected from the group consisting of His231Leu and a valine inserted between Met1 and Ser2.

21. The protein of claim 5, further comprising one or more mutations selected from the group consisting of His231Leu and a valine inserted between Met1 and Ser2.

22. The protein of claim 7, further comprising one or more mutations selected from the group consisting of His231Leu and a valine inserted between Met1 and Ser2.

23. The protein of claim 14, wherein said one or more mutations selected from the group consisting of His231Leu and a valine inserted between Met1 and Ser2.

24. The protein of claim 15, wherein said one or more mutations selected from the group consisting of His231Leu and a valine inserted between Met1 and Ser2.

25. The protein of claim 16, wherein said one or more mutations selected from the group consisting of His231Leu and a valine inserted between Met1 and Ser2.

26. The protein of claim 17, wherein said one or more mutations selected from the group consisting of His231Leu and a valine inserted between Met1 and Ser2.

27. The protein of claim 18, wherein said one or more mutations selected from the group consisting of His231Leu and a valine inserted between Met1 and Ser2.

* * * * *

UNITED STATES PATENT AND TRADEMARK OFFICE
CERTIFICATE OF CORRECTION

PATENT NO.   : 6,194,548 B1
DATED        : February 27, 2001
INVENTOR(S)  : Takashi Osumi et al.

It is certified that error appears in the above-identified patent and that said Letters Patent is hereby corrected as shown below:

Column 4,
Delete "SEQ ID NO: 2".

Signed and Sealed this

Twenty-fifth Day of June, 2002

Attest:

JAMES E. ROGAN
Attesting Officer     Director of the United States Patent and Trademark Office